United States Patent [19]

Osbon et al.

[11] Patent Number: 5,244,453

[45] Date of Patent: Sep. 14, 1993

[54] APPARATUS FOR AUGMENTING MALE POTENCY

[75] Inventors: Robert E. Osbon, Taylors; Philip L. Reid, Duncan, both of S.C.; Julian W. Osbon, Augusta, Ga.

[73] Assignee: Osbon Medical Systems, Inc., Augusta, Ga.

[21] Appl. No.: 991,510

[22] Filed: Dec. 17, 1992

Related U.S. Application Data

[63] Continuation of Ser. No. 880,308, May 5, 1992, abandoned, which is a continuation of Ser. No. 504,354, Apr. 3, 1990, abandoned.

[51] Int. Cl.$^5$ .............................................. A61F 5/41
[52] U.S. Cl. ...................................... 600/38; 600/41
[58] Field of Search ............................ 600/38, 39, 41

[56] References Cited

U.S. PATENT DOCUMENTS

| | | |
|---|---|---|
| D. 47,419 | 4/1915 | Golden . |
| D. 293,473 | 12/1987 | Chaney ................ D24/64 |
| D. 317,504 | 6/1991 | Osbon . |
| D. 317,505 | 6/1991 | Osborn . |
| 594,815 | 11/1897 | Taggart . |
| 823,877 | 6/1906 | Kellogg . |
| 844,798 | 2/1907 | Hawley . |
| 871,622 | 11/1907 | Pettee . |
| 938,808 | 11/1909 | Yount . |
| 1,095,899 | 5/1914 | Macarthy . |
| 1,133,958 | 3/1915 | Henderson . |
| 1,225,341 | 5/1917 | Lederer . |
| 2,068,173 | 1/1937 | Galves .................. 128/79 |
| 2,294,066 | 8/1942 | Baehler ................. 128/158 |
| 2,333,237 | 11/1943 | Erekson ................ 128/327 |
| 2,581,114 | 1/1952 | Larson .................. 128/79 |
| 2,619,964 | 12/1952 | Thaete ................. 128/303 |
| 2,764,160 | 9/1956 | Alexander et al. ..... 128/303 |
| 2,818,855 | 1/1958 | Miller .................. 128/79 |
| 2,874,698 | 2/1959 | Sell .................... 128/79 |

(List continued on next page.)

FOREIGN PATENT DOCUMENTS

| | | | |
|---|---|---|---|
| 158658 | 9/1954 | Australia ..................... | 128/79 |
| 148586 | 7/1985 | European Pat. Off. ......... | 128/79 |
| 36015 | 1/1909 | Fed. Rep. of Germany . | |
| 2057734 | 6/1972 | Fed. Rep. of Germany . | |
| 313836 | of 1934 | Italy . | |
| 347300 | 9/1960 | Italy . | |
| 712163 | 7/1954 | United Kingdom . | |
| 2052266 | 1/1981 | United Kingdom . | |

OTHER PUBLICATIONS

Materials from Chaney Litigation, 32 pages.
Two (2) page insert for "ErecAid" produdct entitled Quick Release Constriction Band.
Six (6) page article entitled "Penile Plethysmography On Impotent Men Using Vacuum Constrictor Devices," Sep. 1988.

*Primary Examiner*—Cary E. O'Connor
*Attorney, Agent, or Firm*—Dority & Manning

[57] ABSTRACT

An improved apparatus for augmenting male potency generally includes a cylindrical vacuum chamber adapted to cover a male sex organ. The vacuum chamber has an open proximal end and a closed distal end. The distal end is tapered to provide an integral ramp for expanding a resilient cincture band onto the outside diameter of the vacuum chamber. A vacuum connector fitting is formed at the base of such ramp for evacuation of the vacuum chamber. Guard flanges help protect the fitting. The proximal end includes a cincture band groove defined about the outside diameter of the vacuum chamber, with a plurality of vent holes formed in the groove and pneumatically interconnecting the exterior of the vacuum chamber with its interior. A cincture band which has been expanded onto the outside diameter of the vacuum chamber and advanced to its proximal end initially resides in the cincture band groove, where it covers and seals the plurality of vent holes. Once desired engorgement is achieved, the cincture band is further advanced onto the base of the user's male sex organ which simultaneously vents negative pressure within the chamber through uncovering of the vent holes. The construction of the cincture band includes a pair of semi-ellipsoidal handles and an enlarged region to be aligned with the urethra of the user's male sex organ so as to relatively reduce urethra constriction for improved seminal fluid discharge.

45 Claims, 3 Drawing Sheets

U.S. PATENT DOCUMENTS

| | | | |
|---|---|---|---|
| 2,942,604 | 6/1960 | Gravelee, Jr. | 128/303 |
| 3,382,873 | 5/1968 | Banich et al. | 128/326 |
| 3,421,504 | 1/1969 | Gibbons | 128/278 |
| 3,455,301 | 7/1969 | Clark | 128/79 |
| 3,461,863 | 8/1969 | Sullinger | 128/79 |
| 3,511,230 | 5/1970 | Strong | 128/79 |
| 3,621,840 | 11/1971 | Macchioni | 128/79 |
| 3,631,853 | 1/1972 | Burdette, Jr. | 128/79 |
| 3,705,580 | 12/1972 | Gauthier | 128/79 |
| 3,718,360 | 2/1973 | Knutzen | 294/27 H |
| 3,726,278 | 4/1973 | Scott | 128/303 |
| 3,744,486 | 7/1973 | Wilson | 128/79 |
| 3,759,253 | 9/1973 | Cray | 128/79 |
| 3,760,810 | 9/1973 | Van Hoorn | 128/326 |
| 3,794,020 | 2/1974 | Bagby | 128/79 |
| 3,799,157 | 3/1974 | McIntire | 128/79 |
| 3,820,533 | 6/1974 | Jones | 128/79 |
| 3,845,760 | 11/1974 | Birman | 128/79 |
| 3,910,262 | 10/1975 | Stoughton | 128/40 |
| 3,989,049 | 11/1976 | Yoon | 128/326 |
| 4,139,007 | 2/1979 | Diamond | 128/138 R |
| 4,175,554 | 11/1979 | Gerow | 128/79 |
| 4,203,432 | 5/1980 | Koch | 128/79 |
| 4,224,933 | 9/1980 | Reiling | 128/79 |
| 4,257,419 | 3/1981 | Goltner et al. | 128/303 |
| 4,291,451 | 9/1981 | O'Neill et al. | 29/235 |
| 4,378,008 | 3/1983 | Osbon, Sr. | 128/79 |
| 4,381,767 | 5/1983 | Finney | 128/79 |
| 4,493,319 | 1/1985 | Polk et al. | 128/303 |
| 4,539,980 | 9/1985 | Chaney | 128/79 |
| 4,548,201 | 10/1985 | Yoon | 128/326 |
| 4,553,300 | 11/1985 | Mancha | 29/235 |
| 4,628,915 | 12/1986 | Chaney | 128/79 |
| 4,641,638 | 2/1987 | Perry | 128/79 |
| 4,671,262 | 6/1987 | West | 128/79 |
| 4,690,135 | 9/1987 | Gerow | 128/79 |
| 4,741,329 | 5/1988 | Marcune | 128/79 |
| 4,753,227 | 6/1988 | Yanuck, Jr. | 128/79 |
| 4,856,498 | 9/1989 | Osbon | 128/79 |
| 4,856,499 | 8/1989 | Kelly | 128/79 |

APPARATUS FOR AUGMENTING MALE POTENCY

This is a continuation of application U.S. Ser. No. 07/880,308, filed May 5, 1992, now abandoned, which is a continuation of U.S. Ser. No. 07/504,354, filed Apr. 3, 1990, now abandoned.

BACKGROUND OF THE INVENTION

The present invention deals in general with improved apparatus for augmenting male potency, and in particular concerns a generally cylindrical vacuum chamber incorporating various advancements as well as particular improvements in cincture band construction.

Vacuum generating devices for augmenting male potency which evacuate a cylinder placed over the male organ, and thereby induce engorgement, are generally known. Likewise, the use of cincture bands or other resilient members to retain such engorgement are also known. See for example U.S. Pat. No. 4,856,498 issued to Osbon, commonly assigned with this application, and entitled "Vacuum Generating And Constriction Apparatus For Augmenting Male Potency." In general, evacuation of the cylinder (once received over the male sex organ) draws blood into the organ so that the flaccid penis becomes erect for sexual intercourse. A constriction device applied to the base or root of the male sex organ operates to retain the erect condition through garroting or cincturing the blood drawn into the engorged organ.

While the foregoing basic operations and related methodology are well-known and to a certain degree effective as one therapeutic approach to male impotence, improvements have been sought in specific operations such as manipulation and use of the various apparatuses. For example, manipulation of resilient cincture bands typically involves expansion of the resilient band and subsequent placement thereof onto the root of the male sex organ. Chaney, U.S. Pat. No. 4,628,915, discloses a cone-like accessory device and associated latchable sleeve. The cone is used to expand an elastic ring onto a sleeve. Thereafter, the sleeve is unlatched from the cone and slipped onto the base of the male sex organ for transfer of the elastic ring thereto. Blood is subsequently massaged into the male sex organ where it is retained by the seated elastic ring.

Chaney, U.S. Pat. No. 4,539,980, also discloses such cone and sleeve combination together with a particular elastic ring with handles for use therewith. Both of the foregoing Chaney devices constitute accessory devices rather than being directly associated with a vacuum chamber, and both use the elastic ring acting in effect as a check valve to prevent the outflow of blood massaged into the male sex organ. Such an arrangement requires a number of separate apparatuses, steps, and operations in order to achieve and retain male sex organ engorgement.

Other practical aspects of various prior art devices have drawbacks and disadvantages which warrant improvement. For example, Yanuck, Jr., U.S. Pat. No. 4,753,227, discloses an erection device and method which requires a valve assembly and means for actuating same into an open position whenever an elastic constriction band is dislodged. The stated purpose of such valve assembly and related requisite means is to equalize pressure within and without the vacuum chamber to facilitate removal of the device from an engorged male sex organ. The constructions by which such objects are achieved with Yanuck involve a plurality of parts which must first be manufactured and assembled, and thereafter perform flawlessly during operation in order to best facilitate withdrawal operations.

While the above Chaney patents, as well as the Chaney U.S. Design Pat. No. 293,473, disclose elastic rings with handles, other prior art devices have often made use of plain circular members for cincturing operations. See for example U.S. Pat. Nos. 3,461,863 to Sullinger; 4,378,008 to Osbon, Sr.; and 4,753,227 to Yanuck, Jr. Commonly assigned U.S. Pat. No. 4,856,498 to Osbon discloses an elastic ring with handle members. Other elastic cincture band devices have sought improvement through considerable elaboration and complexity. For example, Cray, U.S. Pat. No. 3,759,253, with an invention entitled "Human Male Appliance," seeks to restrict the flow of blood from the penis while not materially impeding blood flow to the penis. Cray also discloses a urethra cradle for permitting relatively free egress of seminal fluids. The urethra is the urinary canal. In human males, the urethra also serves as the genital duct for discharge of seminal fluids during climactic expulsion (i.e., ejaculation).

In addition, to the foregoing concerns for practicality, numerous other needs are based on the individual user's physical and subjective requirements, as well as legitimate concerns for privacy, simplicity, and economy while providing apparatuses effective for producing and retaining the desired sexually potent condition (i.e., penile erection).

SUMMARY OF THE INVENTION

The present invention recognizes and addresses various of the foregoing problems, and others, concerning vacuum chamber apparatuses, cincture band devices, and related operations for augmenting male potency. Thus, broadly speaking, a principle object of this invention is improved apparatus for augmenting male potency. More particularly, a main concern is providing an improved vacuum chamber for easy and effective use in augmenting male potency through the initial production of male sex organ engorgement and subsequent retention of such condition.

It is therefore another object of this invention to provide an apparatus which facilitates the loading and expansion of cincture bands integrally with a vacuum chamber type device. More specifically, it is an object to provide an apparatus which improves both efficiency and facility of handling a cincture band, from the initial expansion thereof to its subsequent placement onto the root of a user's male sex organ. The greater the simplicity of use, the more natural the chamber induced erection process feels to the user, resulting in less interruption and greater confidence in the overall therapy.

It is another general object to this invention to provide a vacuum chamber which is automatically vented upon removal of an expanded elastic cincture band therefrom, while at the same time being both simple and effective for manufacture and operation.

Still a further particular object is to provide an improved vacuum chamber apparatus which provides a degree of protection for vacuum connector fittings associated therewith.

While one object is to provide respective features for use in different embodiments, providing an improved vacuum chamber apparatus which combines a number or even all of the foregoing features is yet another present objective. Likewise, it is a present object to provide alternatively for the combination of still further features, such as means for assisting transfer of an expanded cincture band from the vacuum chamber onto the root of a male sex organ, and improvements for better form fitting of the vacuum chamber to the end of a user's male sex organ while also reducing the amount of area to be evacuated. Other additionally alternative features may be selectively incorporated, such as inserts for adapting a given apparatus to suit the physical and subjective comfort and other requirements of a respective user.

Another present object is to provide an improved cincture band device. More particularly, it is desired to provide an elastic band or ring structure which is both readily manufactured and used, while also providing increased urethral comfort. A further object is providing a combination of such an improved cincture band with vacuum chamber means, including alternatively those vacuum chamber means of the improved type disclosed herewith.

Additional objects and advantages of the invention are set forth, or will be apparent to those of ordinary skill in the art, from the detailed description which follows. Also, it should be appreciated that modifications and variations to the specifically illustrated and discussed features hereof may be practiced in various embodiments and uses of this invention without departing from the spirit and scope thereof, by virtue of present reference thereto. Such variations may include, but are not limited to, substitution of equivalent means and features or materials for those shown or discussed, and the functional or positional reversal of various parts or features, or the like.

Still further, it is to be understood that different embodiments, as well as different presently preferred embodiments, of the present invention may include various combinations of presently disclosed features or their equivalents (including combinations thereof not expressly shown or stated). One exemplary such embodiment of the present invention relates to an improved apparatus for augmenting male potency through vacuum-generated engorgement of the male sex organ and subsequent cincture thereof with a cincture band. Such apparatus preferably comprises an elongated, generally cylindrical vacuum chamber adapted to cover a male sex organ. The vacuum chamber is open at a proximal longitudinal end thereof for contact with a user and for passage of the user's male sex organ therethrough into the interior of such chamber. The chamber further integrally defines cincture band expansion means at the opposite longitudinal end thereof for expanding to the outside diameter of such generally cylindrical vacuum chamber a resilient cincture band applied to such expansion means. With such construction, an expanded cincture band (of the present construction or of other types) may be advanced towards the chamber proximal end for user-selected placement over the root of the user's male sex organ for retaining an erect condition thereof otherwise produced. Generally speaking, all of the present vacuum chamber constructions may be practiced in combination with the presently disclosed cincture band construction or with other constructions performing at least a cincturing function.

Another present exemplary embodiment concerns an improved apparatus for augmenting male potency, including a generally cylindrical vacuum chamber adapted to cover a male sex organ, and being open at a proximal longitudinal end thereof as described above. Such proximal end for such embodiment is further adapted for receipt of a cincture band about its outside diameter, and in position so as to be selectively moved onto and elastically fitted about the base of the user's male sex organ when such is engorged. The proximal end of such particular exemplary construction further defines a plurality of vent holes through its outside diameter and in positions so as to be covered and sealed by a cincture band received about the proximal end outside diameter. With the foregoing construction, movement of such cincture band onto the root of a user's male sex organ uncovers the vent holes so as to simultaneously effect automatic venting of negative pressure within the vacuum chamber to facilitate removal of the user's male sex organ from such chamber.

Yet other exemplary constructions comprising present exemplary embodiments relate to an improved vacuum chamber for use in augmenting male potency, comprising a generally cylindrical member having an outside diameter, and having proximal and distal ends adapted for being positioned relatively adjacent to and removed from, respectively, the body of a user. Such distal end is generally closed, while the proximal end is generally open for passage of a user's male sex organ therethrough. Such structure preferably further includes an interior chamber defined within the cylindrical member between the proximal and distal ends thereof, such interior chamber being adapted to be at least partially evacuated with at least a portion of the user's male sex organ introduced therein through the cylindrical member proximal end.

In combination with such exemplary construction, a present exemplary embodiment preferably may further include a cincture band ramp integrally formed in such cylindrical member distal end and operatively interconnecting with such cylindrical member outside diameter. With such arrangement, an elastic cincture band can be enlarged from its at rest condition by forcing same over the distal end ramp therefor. Afterwards, such cincture band received about the cylindrical member outside diameter can be moved along the length thereof to the proximal end for subsequent selected placement over the root of a user's male sex organ to secure an engorged condition thereof as produced with negative pressure created within the interior chamber.

A further particular embodiment making use of the foregoing combination of the generally cylindrical member and an interior chamber, also preferably includes a cincture band groove and a plurality of vent holes. Such cincture band groove is preferably formed in the outside diameter of the cylindrical member adjacent its proximal end, and is adapted for receipt of a cincture band therein for subsequently being selectively moved onto the base of a user's male sex organ so as to cincture an engorged condition of same. The plurality of vent holes are preferably formed in the cincture band groove and through the outside diameter of the cylindrical member so as to interconnect the interior chamber with the exterior of the cylindrical member. With such a construction, a cincture band received in the groove therefor initially seals the vent holes so that negative pressure may be created within the interior chamber with a user's male sex organ therein to induce engorgement of such. Subsequent movement of such cincture band onto the base of the user's male sex organ then automatically uncovers the vent holes and vents to the cylindrical member exterior negative pressure within such interior chamber so as to facilitate withdrawal of the user's engorged male sex organ therefrom.

Still a further present exemplary embodiment making use of the foregoing combination of a generally cylindrical member and an interior chamber, further includes in combination therewith vacuum connector means and guard means. Such vacuum connector means preferably are operatively associated with the cylindrical member distal end for connecting a source of negative pressure with the interior chamber for the production of negative pressure therein. Such guard means are preferably operatively associated with the vacuum connector means for shielding such against damage.

Another present exemplary embodiment is directed to apparatus for improving male potency, such apparatus including an elongated generally cylindrical vacuum chamber, a circumferential groove defined thereabout, and a plurality of vent holes defined in such groove. The preferred elongated generally cylindrical vacuum chamber of such embodiment is of sufficient size to cover a male sex organ, and is open on one end thereof and closed on its opposite end. The circumferential groove is preferably defined about the outside diameter of such vacuum chamber, adjacent its open end, and adapted for receipt of stretchably elastic band means therein. The vent holes are defined in the groove and extending through the vacuum chamber outside diameter for selective pneumatic interconnection of the interior of the vacuum chamber with its exterior. The vacuum chamber closed end is exteriorly tapered from its outside diameter to an end of lesser diameter, and is interiorly rounded for improving form fit with the end of a user's male sex organ and for reducing vacuum chamber interior volume to be evacuated.

Such a foregoing combination of features permits stretchable elastic band means initially applied to the vacuum chamber tapered closed end to be expanded onto the vacuum chamber outside diameter, and subsequently advanced therealong in such expanded condition until residing in the circumferential groove for sealing the vent holes whereby vacuum induced engorgement of a user's male sex organ therein may be accomplished. Subsequent thereto, selective advancement of the expanded elastic band means off the vacuum chamber open end and onto the base of a user's male sex organ received in such vacuum chamber automatically uncovers the vent holes and simultaneously vents negative pressure in the interior of such vacuum chamber to the exterior thereof so as to facilitate withdrawal from the vacuum chamber of the user's engorged male sex organ with such elastic band means applied thereto.

The foregoing exemplary constructions may be practiced, and optionally combined, with cincture band devices in accordance with this invention. One exemplary such embodiment relates to a cincturing device for improving male potency by retaining an engorged condition of the user's male sex organ. Such device preferably comprises a ring of elastic material, having a generally circular outside diameter and inside diameter, with a protruding region defined thereby for receipt of the user's male sex organ urethra; and further comprises handle means integrally formed with peripheral portions of such ring for facilitating manipulation and alignment of same. With such construction, the ring may be elastically fitted to the base of the user's male sex organ for cincturing blood flow therefrom at peripheral areas of the user's male sex organ so as to retain an engorged condition of such organ, while the user's urethra is received in such protruding region therefor so as to decrease stricture of the urethra for improved discharge of seminal fluids.

Those of ordinary skill in the art will better appreciate the features and aspects of such embodiments, and others, upon review of the remainder of the specification.

BRIEF DESCRIPTION OF THE DRAWINGS

A full and enabling disclosure of the present invention, including the best mode thereof, directed to one of ordinary skill in the art, is set forth in the remainder of the specification, which makes reference to the appended figures in which:

FIG. 7 is a top plan view of an exemplary cincture band device in accordance with this invention.

Figure 1:
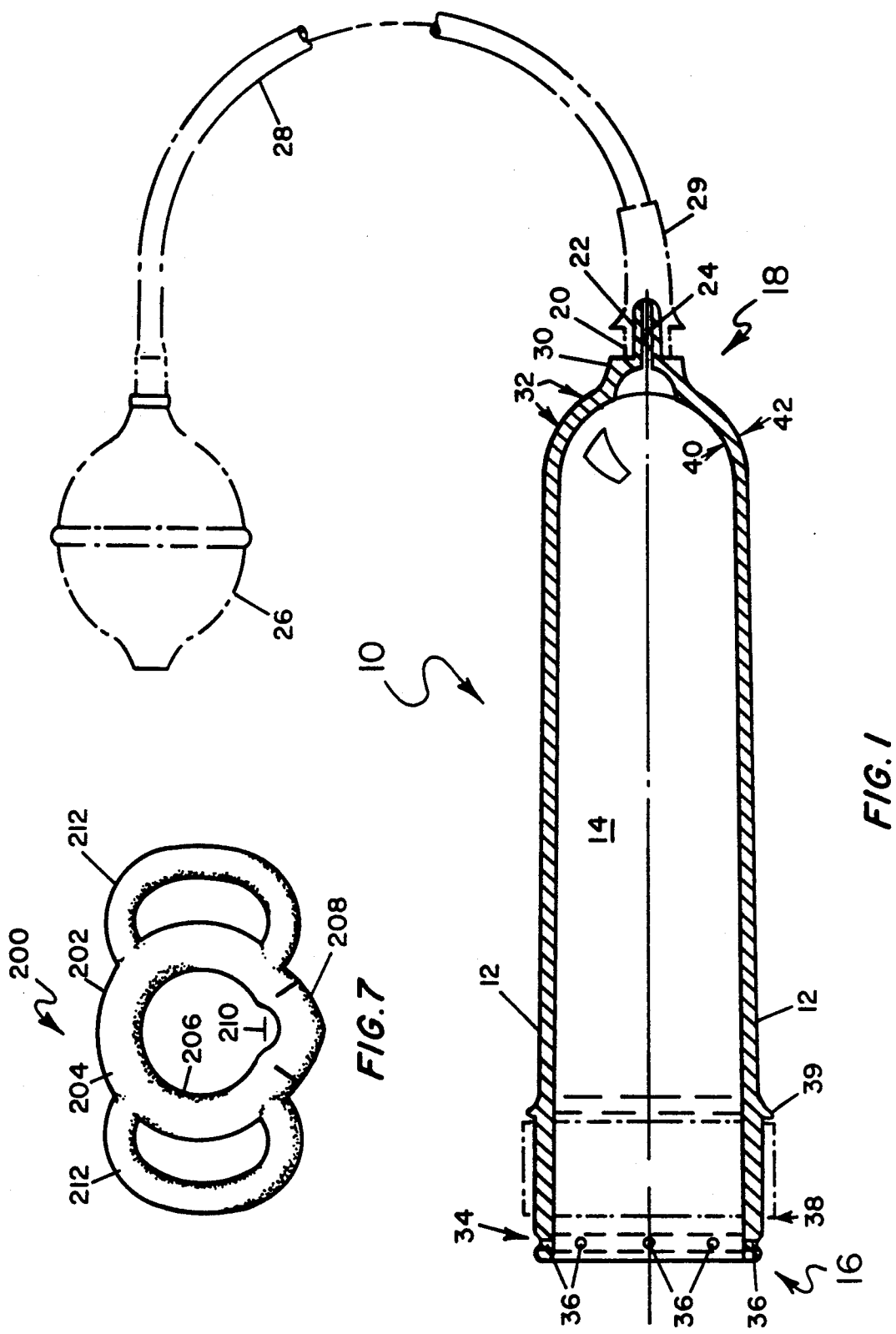
FIG. 1 is a longitudinal cross sectional view of a first embodiment of the present invention incorporating a combination of present features relating to cincture band expansion and automatic venting.

Repeat use of reference characters throughout the present specification and appended drawings is intended to represent same or analogous features or elements of the invention.

DETAILED DESCRIPTION OF THE PREFERRED EMBODIMENTS

Those of ordinary skill in the art will appreciate that the following description is by way of example only, and is intended with reference to the exemplary embodiments and configurations illustrated in the present figures. Furthermore, it should be further appreciated that given illustrations of embodiments incorporate various present features which may be otherwise associated with one another in other embodiments of this invention. For example, present FIG. 1 illustrates an embodiment including cincture band expansion and automatic venting features, while the FIG. 3 embodiment illustrates a combination of cincture band expansion means, vacuum connector fitting means and guard means, and insert means features. FIG. 7 illustrates a present exemplary cincture band which may be used with other aspects of this invention.

FIG. 1 illustrates in side longitudinal cross section one exemplary improved apparatus for augmenting male potency in accordance with the present invention. Such apparatus includes a generally cylindrical member 10 having an outside diameter 12 defined by its circumference. Cylindrical member 10 constitutes a vacuum chamber having an interior chamber 14 within which at least a partial negative pressure is created while a user's male sex organ is at least partially received therein, as well understood by those of ordinary skill in the art without more specific illustration (i.e., the positioning of a male appendage as relates to the present apparatus is understood without direct illustration of such).

A proximal longitudinal end 16 of cylindrical member 10 is generally open for passage of a user's male sex organ therethrough into interior chamber 14. Such end 16 is referred to as proximal because it is brought into contact with a user during use of apparatus 10 while an opposite distal end 18 is generally removed from the body (i.e., the torso) of the user. Distal end 18 is generally closed, but may in preferred embodiments have a passage therethrough defined by vacuum connector means 20 formed therein. Such means 20 may comprise a vacuum connector fitting with a variety of forms, such as an extended stem portion 22 and a central passage 24 therein for the production of negative pressure within chamber 14.

A source of vacuum such as squeeze bulb 26, or virtually any other equivalent means (either power driven or manually actuated) for providing a source of negative pressure, may be interconnected to vacuum connector means 20 via a vacuum hose 28 or the like. Another preferred example is a hand pump device, such as available from Neward Industries of California. Vacuum hose 28 may be connected through a fitting 29 or similar device to vacuum connector means 20. U.S. Pat. No. 4,856,498, the disclosure of which is incorporated herein by reference, illustrates exemplary vacuum pump, hose, and coupling features which would serve the desired functions. Furthermore, such arrangements are generally well known to those of ordinary skill in the art, wherefore further details need not be discussed for an adequate understanding of this invention.

As represented in present FIG. 1, distal end 18 terminates in an end 30 of lesser diameter than outside diameter 12 of vacuum chamber 10. Preferably, for the provision of means integral with vacuum chamber 10 for expanding a cincture band applied thereto, a curved or domed portion 32 is formed between outside diameter 12 and reduced diameter terminus 30. Such cincture band ramp or cincture band expansion means 32 integrally formed with vacuum chamber 10 obviates the need for separate equipment or apparatus for expanding a cincture band for subsequent use.

The foregoing arrangement also advantageously results in automatic application of the expanded cincture band to the outside diameter of vacuum chamber 10, for being further directed therealong towards proximal end 16 until residing in a positioning means 34 for receiving and supporting same. Means 34 preferably comprises a groove formed in the outside diameter 12 of vacuum chamber 10, and adapted to receive a cincture band therein. For clarity in illustration, an exemplary cincture band is shown in later figures. Different cincture band constructions may be practiced in combination with such features of this invention. Elastic bands of the types shown in U.S. Pat. Nos. 4,378,008 and 4,856,498 (both referenced, supra) are two examples, while the further improved band of present FIG. 7 is another acceptable form.

A plurality of vent holes 36 are also formed in vacuum chamber 10 adjacent proximal end 16 thereof, and extend through outside diameter 12 so as to interconnect the exterior of vacuum chamber 10 with its interior, i.e., interior chamber 14. Most preferably vent holes 36 are formed in the same plane as groove 34 (substantially perpendicular to the longitudinal axis of member 10) so as to reside in such groove. By providing a partial toroidal (i.e., doughnut shaped) construction, cincture band groove 34 permits a cincture band received therein to cover and seal the plurality of vent holes 36, thereby enabling the desired creation of at least a partial vacuum within chamber 14 as discussed above.

Once vacuum inducement operations have resulted in the desired level of male sex organ engorgement, a cincture band received in groove 34 (not shown) is ready to be advanced onto the base of the user's male sex organ. Such operation not only cinctures the organ for retaining the engorged condition thereof, but advantageously also simultaneously results in uncovering of the plurality of vent holes 36, thereby resulting in an equalization of the pressure between the exterior and interior of apparatus 10. Such "venting" of negative pressure from within chamber 14 facilitates withdrawal of the user's male sex organ from such chamber. By placement of a plurality of such holes, the venting operation can begin to occur as soon as advancement of any region of the cincture band occurs.

Tubular member 38 (shown in dotted line in present FIG. 1) may be received about outside diameter 12 of apparatus 10, and (under user control) selectively advanced in the direction of proximal end 16 for forcing a cincture band off of apparatus 10 onto the base of the user's male sex organ. Prior to such actuation, stop member 39 provides for controlled positioning of member 38 to ensure adequate space for initial positioning and receipt of a cincture band in groove 34. Such slide means 38 is particularly advantageous for use with cincture bands not having externally extending handles or the like. Cincture bands making use of handles or other similar mechanisms may obviate the need for any slide means 38, since such a cincture band may be readily otherwise manipulated from apparatus 10 onto the user's male sex organ. The cincture of present FIG. 7 is one example of such an advanced cincture band device.

It is well understood by those of ordinary skill in the art that various lubricants, such as petroleum jellies or the like, may be commonly used to facilitate placement and movement of cincture bands (expanded or otherwise) along or onto various surfaces, such as along the length of apparatus 10. Similarly, such lubricants may be used to facilitate enlargement of a cincture band over expansion means 32.

Figure 2:
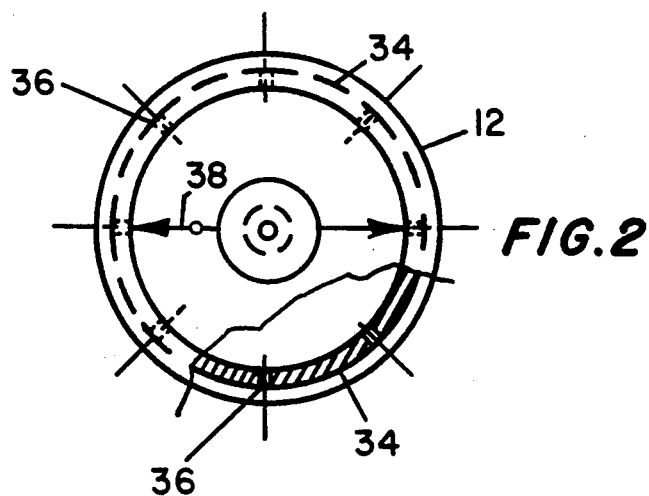
FIG. 2 is an end plan view (with partial cross section) of an open proximal end of the present exemplary embodiment of FIG. 1.

FIG. 2 is an end plan view (with partial cross sectional representations) view of the proximal end 16 of the present embodiment of FIG. 1. The outside diameter 12 of apparatus 10 has defined therein the cincture band groove 34, preferably about the entire circumference thereof. As further represented in FIG. 2, there are a plurality of vent holes 36, generally two or more (and preferably in a range of from about four to about ten holes), spaced preferably equidistantly about the circumference of apparatus 10. The inside diameter 38 of apparatus 10 is preferably in a range centered generally about a two inch diameter. Such inside diameter may be adjustable through the alternative use of other present features such as inserts as discussed below.

Alternative embodiments of this invention may variously incorporate different present features. For example, FIG. 1 illustrates a curved interior terminus 40, generally corresponding with the curved exterior portion 42 of distal end 18. When used, such interior curved terminus 40 results in a reduction of the volume of interior chamber 14 to be evacuated, thus resulting in more efficient application of negative pressure to such chamber and thereby greater efficiency in operations. Such rounded interior terminus also improves form fitting of the distal end of chamber 14 to the end or tip of a user's male sex organ.

Figure 3:
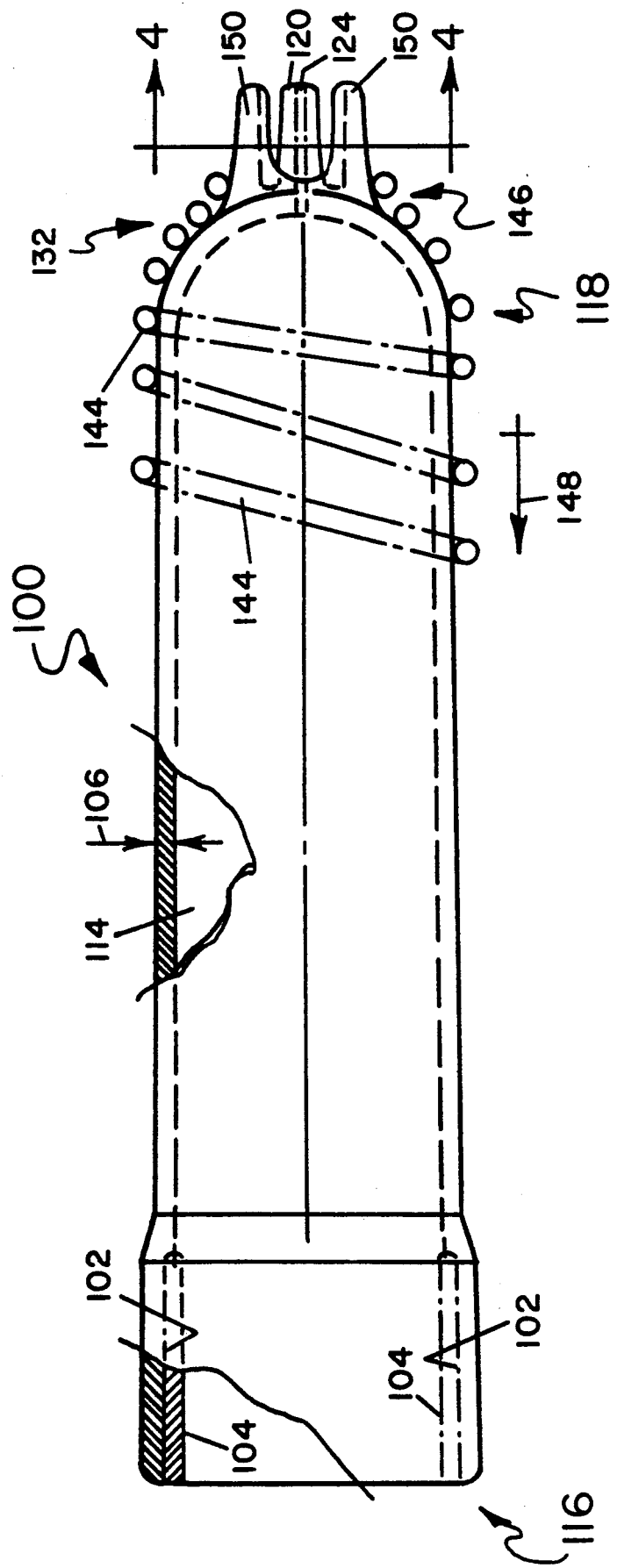
FIG. 3 is a side plan view (with partial cross section) of a second embodiment of the present invention illustrating in combination present features pertaining to cincture band expansion, protection of vacuum connector fittings, and receipt of different adaptive inserts.

FIG. 3 illustrates an alternative embodiment of the present invention, including a different combination of present features from that shown in the exemplary embodiment of present FIG. 1. In particular, the illustrated side plan view of a vacuum chamber 100 incorporates means 102 associated with open proximal end 116 thereof for receiving a tubular insert 104 therein so as to selectively vary the inside diameter of such open end 116 to accommodate differing needs of a respective user. If used in association with a cincture band groove 34 and/or a plurality of vent holes 36 as illustrated in present FIG. 1, such insert 104 preferably should have slots or other openings for cooperation with the vent holes so as to permit the same venting effect as described above.

Insert means 104 may comprise tubular configuration organ adapter means as discussed in commonly assigned U.S. Pat. No. 4,856,498, the disclosure of which is incorporated herein by reference.

Apparatus 100, as well as insert means 104 and the like, are preferably formed of optically transparent materials, particularly plastics, with one preferred example of such being Lexan (a polycarbonate). Transparent Plexiglas acrylic plastic is another example. Preferably the thickness of a side wall 106 is approximately one eight of an inch. One to two inches of the proximal end have preferably about 3/16 of an inch thick walls for added strength. While use of various inserts 104 permits changes in the inside diameter of open proximal end 116, such is preferably within a range of one and one-half to two and one-half inches. The overall length of the interior chamber 114 preferably is in a range centered about a nine inch length, and generally within about seven to about twelve inches.

Distal end 118 of the embodiment of FIG. 3 again includes cincture band expansion means 132 for expanding a cincture band 144 applied thereto. FIG. 3 illustrates a progression of the expansion of such cincture band 144 from where it is first applied to the base region 146 of expansion ramp 132, until it reaches the full outside diameter of side 106 of apparatus 100. As cincture band 144 is advanced in the direction of arrow 148 (such as with including the use of lubricants or the like), the preferably resilient cincture band 144 becomes expanded from its at rest condition shown in the far right position thereof in present FIG. 3. Integral association of means 132 with vacuum chamber 100 results in improved efficiency in cincture band operations because separate devices are not needed for expansion and application of the band, and because the band does not have to be exchanged or transferred from one device to another while in an expanded condition.

Base 146 of ramp 132 coincides with guard means 150 comprising guard flanges disposed about vacuum connector means 120. The primary purpose of such guard means is to prevent damage to the connector fitting 120, particularly from lateral blows such as can occur if apparatus 100 is dropped on the floor, or otherwise accidentally impacted. Such occurrence is particularly not uncommon in light of the amount of lubricant which may be applied to the overall length of the apparatus 100 as cincture band 144 is advanced therealong from distal end 118 to proximal end 116 thereof, and due to the other activities being undertaken by the user.

Figure 4:
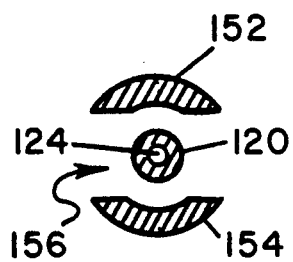
FIG. 4 is a cross sectional view of a portion of the distal end of the exemplary embodiment of present FIG. 3, with such section taken along the line 4—4 indicated therein.
Figure 5:
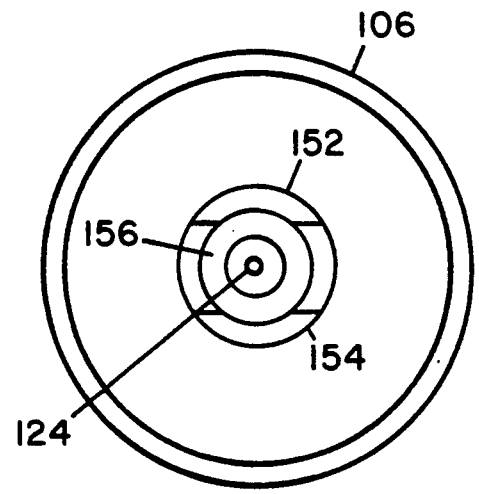
FIG. 5 is an end plan view of the distal end of the present exemplary embodiment illustrated in FIG. 3.

FIG. 4 illustrates a cross sectional view taken along the line 4—4 in present FIG. 3, of a part of distal end 118 of such exemplary apparatus. In particular, the guard means are illustrated as a pair of flange members 152 and 154 extending on either side of a centrally situated vacuum connector means 120. Such structure is further shown in the end plan view of present FIG. 5 illustrating distal 118 of the FIG. 3 embodiment. As illustrated, connector means 120 with its central passage 124 is adequately protected, while at the same time provided with a generally annular region 156 which is completely open and unobstructed for the removable fitting of a coupling thereto, such as coupling 29 illustrated in present FIG. 1. Hence, such arrangement advantageously permits use of numerous standard couplings without interference with the remainder of the structure of present FIG. 3. At the same time, fitting means 120 are protected against damage thereto, which damage would otherwise result in a loss of the usefulness of apparatus 100. In other words, since the usefulness of apparatus 100 is based on its ability to be operated as a vacuum chamber, breaking, or cracking of the extended stem 122 for the vacuum connector means 120 would virtually render the remainder of the apparatus nonuseful for its intended vacuum induced engorgement purposes.

Figure 6:
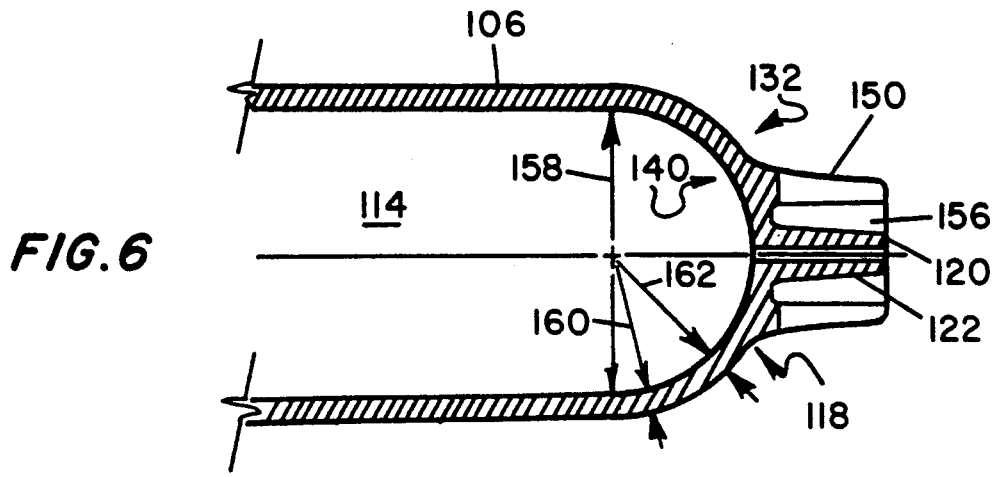
FIG. 6 is a partial, side cross sectional view of the distal end and a portion of the vacuum chamber of the exemplary embodiment of present FIG. 3.

The foregoing arrangement of an integral association of cincture band expansion means 132, guard means 150, and vacuum connector means 120 in association with distal end 118 of the FIG. 3 embodiment are shown in the partial, side cross sectional view of present FIG. 6. Such FIG. 6 shows in greater detail the relationship of the guard flanges to the connector means which they guard, including the region 156 residing about extended stem 122. Still a further aspect of the exemplary illustration shown in FIG. 6 is the interior curved terminus 140 resulting in a reduction of the interior volume to be evacuated, as well as an improved form fit with the end of a user's male sex organ.

Exemplary dimensions of one preferred embodiment include a two inch inside diameter 158 for interior chamber 114, and blended radii of curvature 160 and 162 resulting in the illustrated curved terminus 140. In particular exemplary radius of curvature 160 may be approximately 1.06 inches, with exemplary radius of curvature 162 comprising approximately 0.94 inches. Those of ordinary skill in the art will appreciate that variations within reasonable ranges may be practiced so long as the broader aspects of the present invention are accommodated, particularly where such variations are desired or necessary to accommodate differing physical or subjective requirements of respective users.

Considering the present disclosures of FIGS. 1 through 6 in composite, one embodiment of the present invention results in providing an integral one-piece vacuum chamber which satisfies a plurality of conditions for effective and simple to use operations with a cincture band. In particular, a cincture band may be expanded by cincture band expansion means 32 or 132, and thereafter advanced along the full length of apparatus 10 or 100 until being positioned and/or supported adjacent the proximal end 16 or 116 of a given embodiment. When a plurality of vent holes are used, preferably the cincture band is seated so as to initially seal such vent holes, regardless of the number thereof, whereby subsequent repositioning of the cincture band onto the base of the user's male sex organ results in uncovering of the vent holes for automatically venting the vacuum chamber simultaneous with cincturing operations.

Those of ordinary skill in the art will appreciate that various of the presently disclosed alternative features, such as the guard means 150, the shield means 38, the cincture band groove 34, and insert means 104 may be practiced in various combinations with the foregoing features so as to constitute different exemplary embodiments of this invention. Likewise, different forms of means for generating a vacuum source may be practiced as well as alternative fittings or couplings therefor. Similarly, alternative cincture band arrangements may be practiced with one satisfactory exemplary cincture band comprising device 28 of U.S. Pat. No. 4,856,498, incorporated herein by reference. Another preferred cincture band embodiment is shown in present FIG. 7 and discussed in greater detail hereinafter.

Exemplary cincturing device 200 as illustrated in FIG. 7 comprises an apparatus for improving male potency by retaining an engorged condition of the male sex organ. Preferably, a ring of elastic material 202 has a generally circular outside diameter 204 and inside diameter 206, with a protruding region 208 defined thereby. Such protruding region is adapted for receipt of the user's male sex organ urethra in a receiving portion 210 thereof defined in a given region of inside diameter 206.

Though not specifically illustrated, those of ordinary skill in the art will appreciate that cincturing device 200 may be received about the base of a user's male sex organ with such a rotation and alignment so that the urethra of the user's male sex organ is aligned and received within portion 210 of expanded or protruding region 208. The primary benefit of such arrangement is that there is an improved or greater free discharge of seminal fluids along and from the urethra, or genital duct of the human male, during climactic expulsion. At the same time, the remainder of the elastic ring 202 continues to desirably cincture the engorged condition of the male sex organ.

Preferably, a pair of handle means 212 are provided, centered about peripheral positions on diametrically opposite regions of ring 202. Further preferably, such positions are respectively centered about 90 degrees from the center of protruding region 208, thereby providing convenient and functional handles for a user to manipulate ring 202 through introduction of the user's fingers in the respective handles 212.

Still further preferably, such handles 212 are semi-ellipsoidal, and are integrally formed of elastic material with ring 202. Such handle shape results in improved, more efficient grasping and manipulation of cincturing device 200. The elastic nature of handles 212 also helps the ring 202 to be manually expanded for placement thereof over a flaccid penis. Other methods may be used for expanding ring 202, such as discussed above with reference to cincture band expansion means 32 and 132 of this invention.

Furthermore, it is preferred that the cross section of the circular ring 202 and semi-ellipsoidal handle members 212 be circular. Such prevents the introduction of sharp edges around the male sex organ, and also facilitates manufacture and use of article 200.

It is also preferred that the diameter of handles means 212 be smaller than that of ring 202, so that such handles may be unobtrusive to the extent whereby they may be received within the open proximal end of a vacuum chamber, such as exemplary end 16 illustrated and discussed above, whereby a "second" vacuum may be effected during use of the male potency apparatus. In other words, a "first" vacuum with a given vacuum chamber results in production of a particular level of male sex organ engorgement, preferably followed by cincturing thereof with a device such as apparatus 200. Thereafter, with a device 200 received on the root of the user's male sex organ, the vacuum chamber is removed therefrom, after which the user may assess the level of engorgement (i.e., penile erection).

If additional erection or firmness is desired, a "second" vacuum may be effected by reintroducing the male sex organ to a vacuum chamber. It is at such time that handles 212 of the FIG. 7 embodiment may be unobtrusively and resiliently bent rearwardly towards the root of the user's male sex organ, or otherwise fitted into the open proximal end of the vacuum chamber to permit a "second" vacuum operation while the cincturing device 200 remains seated on the root of the user's male sex organ. Such an arrangement advantageously permits desired fine tuning or increasing of an initial engorged condition, while keeping in place the cincturing device associated with such first engorged condition or level of engorgement.

Still further, it is generally desired that the diameter of circular ring 202 be somewhat greater than that of the respective handles 212, whereby application of a single such cincturing device 200 is adequate for retention of an engorged condition of a user's male sex organ. For example, the diameter of circular ring 202 may be in a range of diameters centered about a thickness of 0.6 centimeters, while the diameter of the respective handle elements 212 is in an exemplary range of diameters centered about a thickness of 0.4 centimeters. Alternatives may be practiced.

The foregoing functional features, advantages, and aspects of cincturing device 200 are totally apart from aesthetic and ornamental features and appeal of the design otherwise also embodied in device 200.

It is a still further embodiment of the present invention that a cincturing device 200 as illustrated in present FIG. 7 may be provided in combination with a vacuum chamber means for producing an engorged condition of a user's male sex organ, for subsequent retention thereof with such elastic or resilient apparatus 200. Vacuum chamber means such as 10 or 100 of the present invention may be practiced in such embodiments, or may be substituted by alternative constructions.

Those of ordinary skill in the art will also appreciate that the foregoing description is by way of example only and not intended as limiting the present invention further set forth by the appended claims.

What is claimed is:

1. An improved apparatus for augmenting male potency through vacuum-generated engorgement of the male sex organ and subsequent cincture thereof with a cincture band, said apparatus comprising an elongated, generally cylindrical vacuum chamber adapted to cover a male sex organ, said vacuum chamber being open at a proximal longitudinal end thereof for contact with a user and for passage of the user's male sex organ therethrough into the interior of said chamber, and said chamber integrally defining cincture band expansion means at the opposite longitudinal end thereof for expanding to the outside diameter of said generally cylindrical vacuum chamber a resilient cincture band applied to said expansion means, said chamber proximal end having generally the same diameter as said vacuum chamber outside diameter, so that a cincture band expanded onto said vacuum chamber outside diameter may be advanced towards and over said chamber proximal end for user-selected placement of such band over the root of the user's male sex organ for retaining an erect condition thereof otherwise produced.

2. An apparatus as in claim 1, wherein said cincture band expansion means comprises tapering defined by said chamber opposite longitudinal end, such tapering interconnecting the outside diameter of said vacuum chamber with a terminus of lesser diameter.

3. An apparatus as in claim 1, further including a rounded interior terminus within said chamber adjacent said opposite longitudinal end thereof for improving form fit with the end of a user's male sex organ and for reducing vacuum chamber interior volume to be evacuated.

4. An apparatus as in claim 1, wherein said vacuum chamber open proximal longitudinal end includes means adapted for receipt of adapter means nestably fit therein for effectively reducing the size of such open proximal end for accommodating different user needs.

5. An apparatus as in claim 1, further comprising slide means received about said vacuum chamber adjacent said proximal end thereof for selected user actuation for moving an expanded cincture band received about said vacuum chamber onto the root of a user's male sex organ.

6. An apparatus as in claim 1, further including an elastic cincture band for application to said expansion means therefor.

7. An apparatus as in claim 1, further including vacuum connector means formed in said opposite longitudinal end of said vacuum chamber for connecting a source of negative pressure with the interior of said vacuum chamber.

8. An apparatus as in claim 7, further including guard means disposed about said vacuum connector means for protecting same, and wherein said vacuum chamber opposite longitudinal end includes a domed portion extending from said guard means to the outside diameter of said vacuum chamber and defining a cincture band ramp for the expansion of a resilient cincture band applied thereto.

9. An apparatus as in claim 8, wherein:
said vacuum chamber comprises optically transparent material; and
the inside diameter of said open proximal end is generally within a range centered about a two inch diameter and the length of said interior of said chamber is generally within a range centered about a nine inch length.

10. An apparatus as in claim 9, further including:
a rounded interior terminus within said chamber adjacent said opposite longitudinal end thereof for improving form fit with the end of a user's male sex organ and for reducing vacuum chamber interior volume to be evacuated; and
slide means received about said vacuum chamber adjacent said proximal end thereof for selected user actuation for moving an expanded cincture band received about said vacuum chamber onto the root of a user's male sex organ; and
wherein said vacuum chamber open proximal longitudinal end includes means adapted for receipt of adapter means nestably fit therein for effectively reducing the size of such open proximal end for accommodating different user needs.

11. An apparatus as in claim 10, further including an elastic cincture band for application to said expansion means therefor.

12. An improved apparatus for augmenting male potency through vacuum-generated engorgement of the male sex organ and subsequent cincture thereof with a cincture band, said apparatus comprising an elongated, generally cylindrical vacuum chamber adapted to cover a male sex organ, said vacuum chamber being open at a proximal longitudinal end thereof for contact with a user and for passage of the user's male sex organ therethrough into the interior of said chamber, and said chamber integrally defining cincture band expansion means at the opposite longitudinal end thereof for expanding to the outside longitudinal end thereof for expanding to the outside diameter of said generally cylindrical vacuum chamber a resilient cincture band applied to said expansion means, whereby such expanded cincture band may be advanced towards said chamber proximal end for user-selected placement over the root of the user's male sex organ for retaining an erect condition thereof otherwise produced, and wherein said cincture band expansion means comprises tapering defined by said chamber opposite longitudinal end, such tapering interconnecting the outside diameter of said vacuum chamber with a terminus of lesser diameter, and said apparatus further comprising vacuum connector means, operatively associated with said vacuum chamber opposite longitudinal end and residing within said lesser diameter terminus thereof, for connecting a source of negative pressure with the interior of said vacuum chamber for the production of negative pressure therein.

13. An apparatus as in claim 12, further comprising guard flanges supported on said vacuum chamber opposite longitudinal end and situated about said vacuum connector means for protecting same.

14. An improved vacuum chamber for use in augmenting male potency, comprising:
a generally cylindrical member having an outside diameter, and having proximal and distal ends adapted for being positioned relatively adjacent to and removed from, respectively, the body of a user, said distal end being generally closed, and said proximal end being generally open for passage of a user's male sex organ therethrough and said proximal end having generally the same diameter as said generally cylindrical member outside diameter;
an interior chamber defined within said cylindrical member between said proximal and distal ends thereof, said interior chamber being adapted to be at least partially evacuated with at least a portion of a user's male sex organ introduced therein through said cylindrical member proximal end; and
a cincture band ramp integrally formed in said cylindrical member distal end and operatively interconnecting with said cylindrical member outside diameter, so that an elastic cincture band can be enlarged from its at rest condition by forcing same over said distal end ramp therefor, whereafter such cincture band received about said cylindrical member outside diameter can be moved along the length thereof to said proximal end for subsequent selected placement over said proximal end and onto the root of a user's male sex organ to secure an engorged condition thereof as produced with negative pressure created within said interior chamber.

15. An improved vacuum chamber as in claim 14, wherein said cylindrical member distal end further defines a curved terminus for said interior chamber.

16. An improved vacuum chamber as in claim 15, further comprising slide means received about said cylindrical member outside diameter adjacent said proximal end thereof for selected user actuation for moving an enlarged cincture band received about said cylindrical member outside diameter onto the root of a user's male sex organ.

17. An improved vacuum chamber as in claim 16, further including:
vacuum connector means at said distal end for interconnecting said interior chamber with a source of negative pressure; and
guard means disposed about said vacuum connector means for protecting same; and wherein
said cylindrical member proximal end is adapted for receiving and retaining a cylindrical insert for adjusting the dimensions of said proximal end inside diameter to satisfy particular fit requirements for each given user;
said cylindrical member comprises optically transparent material; and
the inside diameter of said open proximal end is generally within a range centered about a two inch diameter and the length of said interior chamber is generally within a range centered about a nine inch length.

18. An improved vacuum chamber as in claim 17, having further combined therewith an elastic cincture band to be received about the outside diameter of said cylindrical member.

19. An improved vacuum chamber as in claim 14, wherein said cylindrical member proximal end is adapted for receiving and retaining a cylindrical insert for adjusting the dimensions of said proximal end inside diameter to satisfy particular fit requirements for each given user.

20. An improved vacuum chamber as in claim 14, wherein:
said cylindrical member comprises optically transparent material; and
the inside diameter of said open proximal end is generally within a range centered about a two inch diameter and the length of said interior chamber is generally within a range centered about a nine inch length.

21. An improved vacuum chamber as in claim 14, having further combined therewith an elastic cincture band to be received about the outside diameter of said cylindrical member.

22. An improved vacuum chamber as in claim 14, further including:
vacuum connector means at said distal end for interconnecting said interior chamber with a source of negative pressure; and
guard means disposed about said vacuum connector means for protecting same.

23. An improved vacuum chamber for use in augmenting male potency, comprising:
a generally cylindrical member having an outside diameter, and having proximal and distal ends adapted for being positioned relatively adjacent to and removed from, respectively, the body of a user, said distal end being generally closed, and said proximal end being generally open for passage of a user's male sex organ therethrough;
an interior chamber defined within said cylindrical member between said proximal and distal ends thereof, said interior chamber being adapted to be at least partially evacuated with at least a portion of a user's male sex organ introduced therein through said cylindrical member proximal end;
a cincture band ramp integrally formed in said cylindrical member distal end and operatively interconnecting with said cylindrical member outside diameter, whereby an elastic cincture band can be enlarged from its at rest condition by forcing same over said distal end ramp therefor, whereafter such cincture band received about said cylindrical member outside diameter can be moved along the length thereof to said proximal end for subsequent selected placement over the root of a user's male sex organ to secure an engorged condition thereof as produced with negative pressure created within said interior chamber;
a vacuum connector fitting formed in said cylindrical member distal end for pneumatically interconnecting said interior chamber with a source of negative pressure; and
guard flanges about such vacuum connector fitting for guarding same and defining the base of said cincture band ramp which extends from such base to the outside diameter of said cylindrical member.

24. An improved vacuum chamber for use in augmenting male potency, comprising:
a generally cylindrical member having proximal and distal ends adapted for being positioned relatively adjacent to and removed from, respectively, the body of a user, said distal end being generally closed, and said proximal end being generally open for passage of a user's male sex organ therethrough;
an interior chamber defined within said cylindrical member between said proximal and distal ends thereof, said interior chamber being adapted to be at least partially evacuated with at least a portion of a user's male sex organ introduced therein through said cylindrical member proximal end;
vacuum connector means, operatively associated with said cylindrical member distal end, for connecting a source of negative pressure with said interior chamber for the production of negative pressure therein; and
guard means operatively associated with said vacuum connector means for shielding same against damage.

25. An improved vacuum chamber as in claim 24, wherein said proximal end includes means for receiving an insert for selectively adjusting the inside diameter of said proximal end to accommodate different needs of respective users.

26. An improved vacuum chamber as in claim 24, wherein:
said cylindrical member comprises optically transparent plastic material; and
the inside diameter of said open proximal end is generally within a range centered about a two inch diameter and the length of said interior chamber is generally within a range centered about a nine inch length.

27. An improved vacuum chamber as in claim 24, wherein the interior of said cylindrical member distal end defines a rounded terminus adjacent said interior chamber for form fitting to the end of a user's male sex organ, and for reducing the volume of said interior chamber to be evacuated.

28. An improved vacuum chamber as in claim 24, wherein said vacuum connector means includes a connector fitting having an extended stem portion and a central passage therein for the application of suction thereto so that negative pressure is created in said interior chamber.

29. An improved vacuum chamber as in claim 24, wherein said guard means comprise flange members extending from said cylindrical member distal end so as to laterally shield said vacuum connector means.

30. An improved vacuum chamber as in claim 29, wherein said flange members include at least two flange extensions on diametrically opposite sides of said vacuum connector means, and wherein said distal end is curved from the base of said flange members to the outside diameter thereof so as to form a cincture band ramp against which a resilient cincture band may be applied and enlarged to the outside diameter of such cylindrical member.

31. An improved vacuum chamber as in claim 24, further including cincture band expansion means formed in said cylindrical member distal end for expanding to the outside diameter of said cylindrical member a resilient cincture band applied to said expansion means, whereby such expanded cincture band may be advanced towards said cylindrical member proximal end for subsequently being moved therefrom onto the base of the user's male sex organ.

32. An improved vacuum chamber as in claim 31, wherein said distal end of said interior chamber defines a rounded terminus for reducing the interior volume of said interior chamber to be evacuated, while improving form fit to the end of the user's male sex organ.

33. An improved vacuum chamber as in claim 32, further including:
    actuation means fitted about said cylindrical member outside diameter adjacent said proximal end thereof and responsive to selected user operation for advancing a cincture band received about said cylindrical member outside diameter onto the base of the user's male sex organ; and
    wherein said proximal end includes means for receiving an insert for selectively adjusting the inside diameter of said proximal end to accommodate different needs of respective users;
    said cylindrical member comprises optically transparent plastic material; and
    further wherein the inside diameter of said open proximal end is generally within a range centered about a two inch diameter and the length of said interior chamber is generally within a range centered about a nine inch length.

34. An improved vacuum chamber as in claim 33, further comprising an elastic cincture band adapted to be initially received about said generally cylindrical member and subsequently applied to the base of a user's male sex organ for retaining an engorged condition thereof.

35. An improved vacuum chamber as in claim 24, further including actuation means fitted about said cylindrical member outside diameter adjacent said proximal end thereof and responsive to selected user operation for advancing a cincture band received about said cylindrical member outside diameter onto the base of the user's male sex organ.

36. An improved vacuum chamber as in claim 24, further comprising an elastic cincture band adapted to be initially received about said generally cylindrical member and subsequently applied to the base of a user's male sex organ for retaining an engorged condition thereof.

37. A cincturing device for improving male potency by retaining an engorged condition of the male sex organ, comprising:
    a ring of elastic material, having a generally circular outside diameter and inside diameter, with a protruding region defined thereby for receipt of the user's male sex organ urethra; and
    handle means integrally formed with peripheral portions of said ring for facilitating manipulation and alignment of same;
    whereby said ring may be elastically fitted to the base of a user's male sex organ for cincturing blood flow therefrom at peripheral areas of the user's male sex organ so as to retain an engorged condition of such organ, while the user's urethra is received in said protruding region therefor so as to decrease stricture of the urethra for improved discharge of seminal fluids; and
    wherein said handle means comprise a pair of handles disposed respectively on generally diametrically opposite sides of said ring, and respectively centered about 90 degrees from the center of said protruding region, and wherein said handles are semi-ellipsoidal.

38. A cincturing device for improving male potency by retaining an engorged condition of the male sex organ, comprising:
    a ring of elastic material, having a generally circular outside diameter and inside diameter, with a protruding region defined thereby for receipt of the user's male sex organ urethra; and
    handle means integrally formed with peripheral portions of said ring for facilitating manipulation and alignment of same;
    whereby said ring may be elastically fitted to the base of a user's male sex organ for cincturing blood flow therefrom at peripheral areas of the user's male sex organ so as to retain an engorged condition of such organ, while the user's urethra is received in said protruding region therefor so as to decrease stricture of the urethra for improved discharge of seminal fluids; and
    wherein the thickness of said ring is greater than that of said handle means, whereby application of a single such cincturing device is adequate for retention of an engorged condition of a user's male sex organ.

39. Apparatus for improving male potency through vacuum induced engorgement of a male sex organ and subsequent constrictive retention of such condition with stretchable elastic band means, said apparatus including:
    an elongated, generally cylindrical vacuum chamber of sufficient size to cover a male sex organ, said chamber being open on one end thereof and closed on the opposite end with said closed end being exteriorly tapered from its outside diameter to an end of lesser diameter, and said closed end being interiorly rounded for improving form fit with the end of a user's male sex organ and for reducing vacuum chamber interior volume to be evacuated;
    a vacuum connector fitting incorporated into said vacuum chamber tapered closed end for the induction of negative pressure within said vacuum chamber; and at least one guard flange disposed adjacent said vacuum connector fitting for protecting same;

whereby stretchable elastic band means may be initially applied to said vacuum chamber tapered closed end, expanded onto the vacuum chamber outside diameter, and advanced therealong in such expanded condition until residing adjacent said open end so that vacuum induced engorgement of a user's male sex organ within said vacuum chamber may be achieved, and further whereby subsequent selected advancement of such expanded elastic band means off said vacuum chamber open end and onto the base of a user's male sex organ received in such vacuum chamber constrictively retains the induced engorgement upon withdrawal from the vacuum chamber of the user's engorged male sex organ with such elastic band means applied thereto.

40. An apparatus as in claim 39, wherein said open end of said cylindrical vacuum chamber is adapted for receipt of a tubular insert so as to selectively vary the inside diameter of such open end to accommodate differing needs of a respective user.

41. An apparatus as in claim 40, further comprising:
slide means received about said cylindrical vacuum chamber for selectively advancing expanded elastic band means from said vacuum chamber outside diameter onto the base of the user's male sex organ; and wherein said apparatus comprises optically transparent plastic material; and wherein the inside diameter of said cylindrical vacuum chamber open end is generally in a range of from about one and one-half to two and one-half inches, and the axial length of said cylindrical vacuum chamber is in a range generally from about seven to about twelve inches.

42. An apparatus as in claim 41, further comprising stretchable elastic band means.

43. An apparatus as in claim 39, wherein said apparatus comprises optically transparent plastic material, and wherein the inside diameter of said cylindrical vacuum chamber open end is generally in a range of from about one and one-half to two and one-half inches, and the axial length of said cylindrical vacuum chamber is in a range generally from about seven to about twelve inches.

44. An apparatus as in claim 39, further comprising slide means received about said cylindrical vacuum chamber for selectively advancing expanded elastic band means from said vacuum chamber outside diameter onto the base of a user's male sex organ.

45. Apparatus as in claim 39, further comprising stretchable elastic band means.

* * * * *

UNITED STATES PATENT AND TRADEMARK OFFICE
CERTIFICATE OF CORRECTION

PATENT NO. : 5,244,453

DATED : September 14, 1993

INVENTOR(S) : OSBON et al.

It is certified that error appears in the above-identified patent and that said Letters Patent is hereby corrected as shown below:

On title page, item [75]

delete "Philip L. Reid, Duncan, both of"

Signed and Sealed this

Thirty-first Day of January, 1995

Attest:

BRUCE LEHMAN

Attesting Officer      Commissioner of Patents and Trademarks